Figure 1:
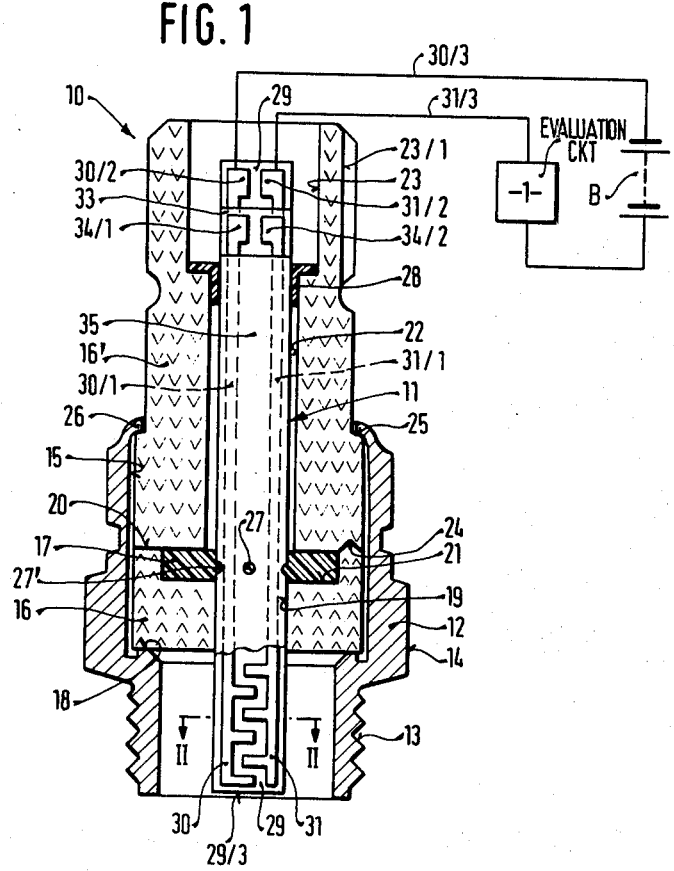

United States Patent [19]
Muller et al.

[11] 4,277,323
[45] Jul. 7, 1981

[54] ELECTROCHEMICAL OXYGEN SENSOR, PARTICULARLY FOR USE IN THE EXHAUST SYSTEM OF AUTOMOTIVE-TYPE INTERNAL COMBUSTION ENGINES

[75] Inventors: Klaus Muller, Tamm; Helmut Maurer, Schwieberdingen; Ernst Linder, Mühlacker; Franz Rieger, Aalen; Bodo Ziegler, Stuttgart, all of Fed. Rep. of Germany

[73] Assignee: Robert Bosch GmbH, Stuttgart, Fed. Rep. of Germany

[21] Appl. No.: 121,600

[22] Filed: Feb. 14, 1980

[30] Foreign Application Priority Data

Mar. 9, 1979 [DE] Fed. Rep. of Germany ....... 2909201

[51] Int. Cl.$^3$ ............................................. G01N 27/58
[52] U.S. Cl. .................................................. 204/195 S
[58] Field of Search ............................ 204/1 S, 195 S

[56] References Cited

U.S. PATENT DOCUMENTS

| | | |
|---|---|---|
| 3,691,023 | 9/1972 | Ruka et al. ......................... 204/195 S |
| 3,719,564 | 3/1973 | Lilly et al. ......................... 204/195 S |
| 4,107,019 | 8/1978 | Takao et al. ....................... 204/195 S |
| 4,145,272 | 3/1979 | Nakamura et al. ................ 204/195 S |
| 4,157,282 | 6/1979 | Riddel ................................ 204/195 S |
| 4,157,948 | 6/1979 | Maurer ............................... 204/195 S |
| 4,177,125 | 12/1979 | Barnabe ............................. 204/195 S |

FOREIGN PATENT DOCUMENTS

| | | |
|---|---|---|
| 2304464 | 8/1974 | Fed. Rep. of Germany ....... 204/195 S |
| 2709173 | 9/1978 | Fed. Rep. of Germany ....... 204/195 S |
| 2718907 | 11/1978 | Fed. Rep. of Germany ....... 204/195 S |
| 2826515 | 1/1979 | Fed. Rep. of Germany . |

Primary Examiner—G. L. Kaplan
Attorney, Agent, or Firm—Frishauf, Holtz, Goodman & Woodward

[57] ABSTRACT

To improve the response speed of an electrochemical oxygen sensor, particularly for automotive use, to sense the oxygen content in exhaust gases, and which can be operative either as a polarographic sensor (requiring application of a voltage thereto), or as a potentiometric sensor (having one catalytically active electrode and another which is less catalytically active), an elongated insulating carrier plate (29), for example of a ceramic, has layer electrodes (30, 31) applied to one major surface thereof and a layer of solid electrolyte material (32) over the electrodes, so that the electrodes will be embedded in the solid electrolyte material. The carrier plate (29) is of a material pervious to oxygen molecules. A gas-impervious insulating cover (33), for example of a ceramic glass, covers the layer of solid electrolyte material (32). A heating element (34) protected by a protective cover (35), for example of aluminum oxide, can be applied against the gas-impervious cover layer (33).

11 Claims, 2 Drawing Figures

ELECTROCHEMICAL OXYGEN SENSOR, PARTICULARLY FOR USE IN THE EXHAUST SYSTEM OF AUTOMOTIVE-TYPE INTERNAL COMBUSTION ENGINES

Reference to related publications:
German Disclosure Document DE-OS No. 28 26 515
U.S. Pat. No. 4,157,282, Riddel
U.S. Ser. No. 121,632, filed Feb. 14, 1980, MULLER et al
U.S. Ser. No. 6,093, filed Jan. 24, 1979, CIP of Ser. No. 885,368, filed Mar. 13, 1978, Dietz, both assigned to the assignee of this application. Ser. No. 885,368 is now abandoned and refiled under continuation application U.S. Ser. No. 213,049, filed Dec. 4, 1980.

The present invention relates to an electrochemical sensor, and more particularly to a sensor which determines the oxygen content in gases, especially gases resulting from a combustion process, and having its primary application to determine the oxygen content in the exhaust gases from internal combustion engines, for example of the automotive type.

BACKGROUND AND PRIOR ART

Various types of oxygen sensors have been proposed—see the referenced German Disclosure Document DE-OS No. 28 26 515, and U.S. Pat. No. 4,157,282, Riddel. DE-OS No. 28 26 515 relates to a sensor which has an essentially flat substrate made of electrically insulating material, or a material which, at least, has an electrically insulating surface. The substrate forms an elongated rectangular plate-like element and a material which responds to the composition of the surrounding atmosphere, for example $ZrO_2$ can be placed on the electrodes which, on the side of the substrate, can extend in interleaved or interdigited form, or in other configurations. U.S. Pat. No. 4,157,282 is directed to maintain the air/fuel mixture supplied to an internal combustion engine at stoichiometric level by directing of stream of exhaust gases simultaneously across two opposite major faces of a zirconium dioxide solid electrolyte body to establish an output voltage between catalytic and non-catalytic gas-pervious electrodes which are, respectively, applied on faces of the body, to then derive a non-equilibrium oxygen content in the gases as a reference atmosphere and to then control the air/fuel mixtures in response to the electrical signal from the sensor. Sensors of these types require relatively long time until they reach their respective necessary operating temperature of about 700° C.; the sensors can be heated, yet the time required for the sensors to reach operating temperature is comparativey long in spite of the low heat capacity of the sensor element itself.

THE INVENTION

Briefly, it is an object to construct a sensor in such a manner that it has short response time, that is, to so construct the sensor that it rapidly will reach its working or normal operating temperature, which is rugged, and adapted to the rough service use encountered in automotive applications.

Briefly, the sensor element itself is a body of solid electrolyte material, for example zirconium dioxide, which is applied to one surface region of an elongated insulated carrier plate or substrate, for example a ceramic. Electrodes are embedded in the electrolyte body and can extend as conductive paths applied to a face of the insulating plate to the terminal end thereof for connection to external conductors. The carrier plate is pervious to oxygen molecules, so that oxygen molecules can pass therethrough to reach the electrodes embedded in the solid electrolyte body and the electrolyte body itself. The obverse side of the solid electrolyte body is covered with a gas-impervious coating which, preferably, also extends around the lateral or narrow sides of the carrier plate and the narrow sides of the solid electrolyte body itself. The gas-impervious cover, which is insulating, may for example be a ceramic glass or the like. If desired, and if required to reach operating temperature rapidly, a heating element can be positioned against the insulating coating, for example in the form of a meandering circuit path applied to yet another support plate.

The sensor has the advantage that its heat capacity is decreased beyond that obtainable from other structures, so that, due to the extremely low heat capacity, the sensor will reach operating temperature rapidly and sooner than previously thought possible. Applying the solid electrolyte body as a layer or element on one surface of the carrier permits shaping the carrier in selected regions opposite the solid electrolyte body in suitable manner to increase the response sensitivity of the sensor element both in continued operation as well as during start-up.

Figure 2:
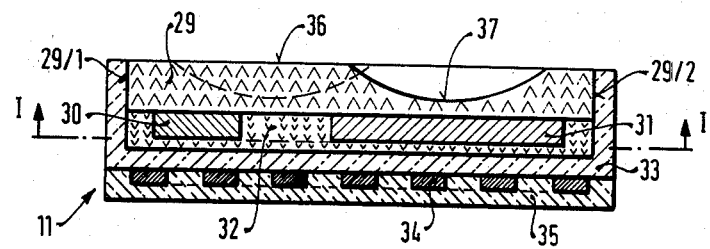

Drawings, illustrating a preferred example, wherein:

FIG. 1 is a longitudinal highly schematic cross-sectional view through a sensor in accordance with the present invention, to an enlarged scale, and showing the sensor element at the region adjacent the sensing portion thereof sectioned along line I—I of FIG. 2; and FIG. 2 is a cross section, to yet a still greater enlarged scale, of the sensing element along line II—II of FIG. 1.

The sensor 10 of FIG. 1 is shown in the form designed for sensing of the oxygen content of exhaust gases from an automotive-type internal combustion engine. Essentially, it consists of the sensor unit 11 itself, which is located within a metallic housing 12, constructed to fit into a portion of the exhaust system of the engine. It has an external thread 13, and an external hexagonal surface 14 for application of a wrench thereto. The housing 12 has a longitudinal bore 15 in which holding elements 16, 16' are located to fix the sensor element 11 in position. A seal 17 seals the sensor element within the opening. The housing 12 has a shoulder 18 internally of its bore 15 on which holder 16 is placed. Holder 16 is a disk of insulating material, for example a ceramic. Holder 16 has a central opening 19 to permit passage of the sensor element 11 therethrough. At its upper side 20, and in the region of the opening 19, a recess 21 is formed in which the seal 17 is received in order to position the sensor element in sealed, gas-tight relationship therein. Seal 17 may be a cement, glass, or the like. The upper side or surface 20 of the holder 16 is engaged by the essentially cylinder-shaped ceramic holder element 16' which, at its lower side, positions the seal 17. The holder 16' has a longitudinal opening 22 to receive the sensor element 11. The portion of the holding element 16' remote from the sensing gas is formed with an enlarged opening 23 into which the portion of the sensor element 11 which is remote from the exhaust gas can extend. In order to ensure proper positioning of the holder 16' with respect to the holder 16, the upper surface 20 of the holder 16 is formed with a projection 24 which fits into a matching recess in the holder 16'. The outer side of the holder 16' is formed with an abutment shoulder 25 which is engaged by an in-turned, rolled-in edge 26 of the housing 12. Thus, the holder elements 16, 16' are securely held within housing 12, with the seal 17 therebetween. To determine the position of the sensor element within the opening 19, or 22, respectively, the sensor element is formed with at least one transverse hole 27 and/or recesses 27' which can be set in or anchored together with the seal 17. The sensor element 11 is additionally held in position by a collar 28 located at the far end thereof and which fits into the holder 16' from the recess 23 thereof and into the longitudinal opening 22. Collar 28, preferably, is of plastic, for example a silicone rubber. Temperature compensation elements are preferably also used in order to compensate for different temperature coefficients of expansion of the respective elements. Such compensation elements are not shown since they can be employed in any well known and suitable manner; further, additional seals which may be interposed between the seal 17 and the collar 28 have been omitted from the drawings; they can be used if required, depending on the physical size of the sensor element itself. The outer side of the holder 16' has a groove 23/1 formed therein to permit orientation of the position of a connecting element to effect electrical connection to the respective electrodes of the sensor unit 11.

The sensor unit 11 (see particularly FIG. 2) has a carrier 29 which consists of an elongated plate of a porous, electrically insulating material, for example of ceramic. It has a thickness of, for example, about 0.6 mm, and a width of about 5 mm. The carrier or support plate 29 has a narrow side 29/3 at the end exposed to the gas; the side 29/3 approximately matches the end of the housing 12 and thus does not necessarily require additional protecting shields, or other elements to protect the sensor unit 11 against temperature shocks and particles within the sensing gas which might impinge thereon.

One major surface of the carrier 29 has a pair of electrodes 30, 31 and connecting conductive tracks or paths 30/1, 31/1 applied thereto. The paths 30/1, 31/1 terminate in connecting terminals 30/2, 31/2 (FIG. 1). The electrodes, the conductive strips and the terminals can be made in accordance with any well known and suitable process, for example by printing, rolling-on, or the like. The electrodes 30, 31 are comb-shaped and interdigited or interleaved. Other configurations for the electrodes may be used. The individual projections or tines of the combs consist of a platinum layer of about 7 $\mu$m thickness. The conductive paths 30/1, 31/1, as well as the terminals 30/2, 31/2 can also consist of platinum and be integral with the electrodes.

The sensor can be operated as a polarographic sensor as described, for example, in U.S. application Ser. No. 6,093 of Jan. 24, 1979, Dietz, assigned to the assignee of the present application, and if so operated, the electrodes 30, 31 are connected over the conductive paths 30/1, 31/1 and terminals 30/2, 31/2 to conductors 30/3, 31/3 which, in turn, are connected to an evaluation circuit[1]/and to a source of voltage, preferably regulated, and schematically illustrated by battery B.

A solid electrolyte element 32 is positioned between the electrodes 30, 31. The solid electrolyte 32 is a body of material which conducts oxygen ions, and for example consists of stabilized zirconium dioxide. It can be applied by a printing application, positioned between the interdigited electrodes 30, 31. In an actual practical application, the solid electrolyte body can extend beyond the outer sides of the electrodes 30, 31 and may even extend over the major surface of the carrier 29 which is remote from the electrodes 30, 31 as well as extending around the carrier itself. A gas-impervious insulating layer 33 is applied over the electrodes and over the narrow sides 29/1, 29/2, 29/3 of the carrier 29. The gas-impervious insulating layer 33 may, for example, consist of ceramic glass, and have a thickness of about 20 $\mu$m. The insulating layer 33 also covers the electrodes, the space therebetween and the electrically conductive tracks 30/1, 31/1 to the end portion of the sensor, leaving only the terminal ends 30/2 and 31/2 uncovered for connection to external connecting lines.

As shown in FIG. 2, the structure basically is a carrier plate 29, on which electrodes 30, 31 ar applied, for example by printing and solid electrolyte material 32 applied between the interdigited or interleaved electrodes, for example by a printing process, in which the solid electrolyte material also may cover the electrodes and reach at the outside therearound. The solid electrolyte material is sealed by the insulating cover 33.

A layer-like heating element 34 is located on the insulating layer 33 in the region of the electrodes 30, 31. Heater element 34 may consist of a conductive track of platinum, arranged in zig-zag or meander form; which the platinum tracks have a thickness of about 10 $\mu$m. It is connected to terminals 34/1, 34/2 over conductive tracks or paths similar to tracks 30/1, 31/1 and not further illustrated. To protect the heater element against oxidation and burn-through, heater element 34 and the conductive tracks (not further identified) are protected by an electrical insulating layer 35 which entirely covers the heater element. Layer 35 may, for example, consist of aluminum oxide of a thickness of about 15 $\mu$m. Heater element 34 is separated from the solid electrolyte body 32 only by the thin insulating layer 33 and thus can rapidly heat the solid electrolyte 32 while requiring only comparatively low heating power. Thus, the solid electrolyte body 32 will rapidly reach the working temperature of about 700° C., and to be maintained thereat.

The support 29 has a such a porosity that it provides a predetermined diffusion resistance to oxygen molecules. The requisite porosity can be obtained by, for example, using suitable materials which form interstices or voids, for example by utilizing organic binders, by controlling a compression process, or by suitable heat treatment. Additionally, the diffusion resistance of the carrier 29 can be accurately determined by forming depressions 37 in the major plane surface 36 exposed to the gas to be sensed. These depressions 37, which can be mechanically made, for example by grinding, can be applied in the region of the electrodes 30, 31 after the sensor has been made; they may be of any desirable and suitable form; preferably, however, they are formed as small or shallow blind bores or blind slits, that is, slits which do not reach entirely through the body 29 and to the electrodes 30, 31 themselves.

All electrodes, not only those previously referred to, namely the electrodes 30, 31, may be applied by any well known manner, for example by printing, rolling, dipping, or the like. After application, the entire sensor unit 11 is integrated by sintering.

The sensor described operates in accordance with polarographic measuring prnciples. The sensor structure can also be utilized in connection with potentiometric sensors described, for example, in the referenced U.S. Pat. No. 4,157,282, Riddel. If the sensor is to be operated in this manner, then the voltage source B can be eliminated since the sensor, then, will itself act as an electrochemical cell and provides output signals in form of varying voltages, to be evaluated in the evaluating circuit 1. In this case, one of the two electrodes 30, 31 must be so arranged that it can catalyze the gas equilibrium. This can be one porous platinum electrode, as used also in a polarographic sensor. The other electrode then must be made of a material of less catalytic activity, for example gold. The porous support plate 29 then acts solely as a protective layer for the electrodes 30, 31 to protect them with respect to the hot gases, the oxygen composition of which is to be measured. Thus, the plate 29 can be made thinner than described or can be formed with additional recesses or depressions 37 than would normally be used with a polarographic sensor.

Manufacturing processes well known in industry, and particularly mass production processes, can be used to make sensor elements as described, and the particular structure is especially suitable for mass production manufacture. The sensors, nevertheless, have high response speed and response sensitivity and require only a minimum of heating power to bring them to operating temperature and to maintain them at operating temperature.

Various changes and modifications may be made within the scope of the inventive concept.

A suitable heating system is described in U.S. Pat. No. 4,033,170 (Kawamura et al).

We claim:

1. Electrochemical oxygen sensor, and particularly to determine the oxygen content in the exhaust gases in a combustion process, for example from an internal combustion engine comprising an electrically insulated elongated carrier plate (29) having one end portion exposed to the gases, said carrier plate being of a material pervious to oxygen molecules;

a layer of solid electrolyte material (32) secured to the carrier plate on one major surface thereof, said carrier plate providing both a support substrate and a path for oxygen molecules to said layer electrolyte material;

layer-like electrodes embedded in the solid electrolyte material and located on one major surface of the insulating carrier plate;

insulating connecting paths (30/1, 31/1) connected to said electrodes and extending to the other end portion of the carrier plate to permit electrical connection thereto;

and a gas-impervious insulating cover (33), applied to the major side of the solid electrolyte body remote from its side which is secured to the carrier plate, and entirely covering the surfaces of the solid electrolyte body not facing said carrier plate.

2. Sensor according to claim 1, wherein the gas-impervious insulating cover (33) extends around and on the lateral narrow sides (29/1, 29/2, 29/3) of the carrier plate (29).

3. Sensor according to claim 1, wherein the carrier plate (29) is formed with depressions or recesses (37) at its major surface (36) parallel to said one major surface.

4. Sensor according to claim 3, wherein the depressions or recesses (37) are positioned in the region of the location of the electrodes (30, 31) and are dimensioned to provide a predetermined gas diffusion resistance to oxygen molecules of the portion of the solid electrolyte plate between the free surface thereof and the electrodes therebeneath.

5. Sensor according to claim 1, further including a layer-like heating element (34) applied to the gas-impervious insulating cover (33).

6. Sensor according to claim 5, further comprising an electrical insulating protective layer (35) covering the layer-like heating element (34).

7. Sensor according to claim 1, further including a housing (12) of metal formed with a longitudinal opening (15) therein;

said carrier plate (29) being fitted in said housing;

a seal (17) sealing the carrier plate (29) with the electrodes (30, 31) into the housing leaving said one end portion exposed;

said electrically connecting paths (30/1, 31/1) extending through said seal and providing electrical connection from said electrodes and said one end portion to the other end portion of the elongated insulating carrier plate (29).

8. Sensor according to claim 1, wherein said sensor is a polarographic sensor;

and connecting terminals (30/2, 31/2) are provided connected to said electrically connecting paths (30/1, 31/1) to apply an electrical voltage to said electrodes, the carrier plate (29) having a predetermined diffusion resistance with respect to the penetration of oxygen molecules therethrough and to the electrodes.

9. Sensor according to claim 1, wherein the sensor is a potentiometric measuring cell, one of the electrodes being of a material providing for catalyzing the gas equilibrium thereon, the other electrode having lesser or no catalytic function;

and further including contact terminal (30/2, 31/2) connected to said conductive paths (30/1, 31/1) for connection of evaluation circuitry evaluating the output voltage of said sensor cell.

10. Sensor according to claim 1, wherein the electrically insulating carrier plate (29) comprises a porous, electrically insulating ceramic having a thickness in the order of about 0.6 mm, and a width in the order of about 5 mm;

at least one of the electrodes comprises platinum;

and wherein the gas-impervious insulating cover (33) comprises a ceramic glass having a thickness in the order of about 0.02 mm.

11. Sensor according to claim 10, further including a heating element (34) applied to said gas-impervious cover (33);

and an electrical insulating layer having a thickness in the order of about 0.015 mm forming a protective cover for said heating element.

* * * * *